United States Patent [19]

Onat

[11] 4,114,625
[45] Sep. 19, 1978

[54] ANTI-VOMITING, ANTI-ASPIRATING ORAL-NASAL GASTRIC TUBE

[76] Inventor: Mustafa V. Onat, Box 7, Saint George, Me. 04857

[21] Appl. No.: 746,778

[22] Filed: Dec. 2, 1976

[51] Int. Cl.² .................................................. A61M 25/00
[52] U.S. Cl. ........................................ 128/348; 128/276; 128/349 B
[58] Field of Search ............................. 128/348–351, 128/240–241, 246, 325, 276

[56] References Cited

U.S. PATENT DOCUMENTS

| | | | |
|---|---|---|---|
| 1,696,018 | 12/1928 | Schellberg | 128/240 |
| 2,845,930 | 8/1958 | Brown | 128/348 |
| 2,981,254 | 4/1961 | Vanderbilt | 128/350 R |
| 3,046,988 | 7/1962 | Moreau et al. | 128/349 B X |
| 3,144,868 | 8/1964 | Jascalevich | 128/350 R |
| 3,885,567 | 5/1975 | Ross | 128/350 R X |

*Primary Examiner*—Dalton L. Truluck

*Attorney, Agent, or Firm*—Sughrue, Rothwell, Mion, Zinn and Macpeak

[57] ABSTRACT

The oral-nasal gastric tube includes three side-by-side passages disposed within a single tube. Two of the tubes branch outwardly from the main tube at one end to facilitate the attachment of one of the tubes to a suction attachment and a pressurized air source respectively. The third tube can be left open to the atmosphere to act as a pressure equalizer or can be utilized for the introduction of medicine or medical devices. The tube attached to the suction attachment and the pressure equalizer tube each terminate in a plurality of apertures adjacent the end of the main tube for supplying air to the body cavity as fluids are being drawn out through the suction tube. The tube attached to the pressurized air source terminates in a balloon which extends about the periphery of the main tube at a point spaced from the end of the main tube above the perforations.

4 Claims, 5 Drawing Figures

ANTI-VOMITING, ANTI-ASPIRATING ORAL-NASAL GASTRIC TUBE

BACKGROUND OF THE INVENTION

1. Field of the Invention

The present invention is directed to an oral-nasal gastric tube adapted to be inserted through the oral or nasal passages into the stomach and more specifically to a tube which will permit the equalization of pressure within the stomach during removal of the contents while simultaneously preventing the vomiting of the contents of the stomach to the esophagus and aspiration into the airways during anesthesia.

2. Prior Art

The use of esophageal tubes for introducing medication into the stomach or for removing the contents of the stomach are old and well known in the art. Although some of these tubes utilize inflatable balloons for blockage purposes there is no disclosure of any means for equalizing the pressure within the stomach while suction is being applied to the tube for the purpose of removing the contents of the stomach. Other stomach tubes are known which provide drainage and feeding functions but such tubes are designed to be inserted directly through the abdominal wall to the stomach. Such tubes are inserted before the end of surgery and are sutured to the stomach wall for an extended period of time subsequent to gastric surgery.

Multiple passage catheters are also known but these catheters are designed and used for urological purposes only.

SUMMARY OF THE INVENTION

The present invention provides a unique gastric tube which will permit the equalization of pressure within the stomach during the removal of the contents of the stomach by suction while simultaneously preventing vomiting of the stomach contents to the esophagus and aspiration into the airways during anesthesia.

The present invention accomplishes the foregoing multiple functions by using a single tube having three side-by-side separate independent passages therein. A suction device may be connected to one of the passages at one end and the opposite end of the passage is provided with a plurality of apertures. The pressurized air source is connected to a second passage which terminates in an inflatable cuff or annular balloon which extends about the periphery of the main tube at a point spaced from the end of the main tube above the perforations. The third tube is coextensive in length with the first tube and can be left open to the atmosphere at one end while the other end is provided with a plurality of apertures adjacent the apertures in the first tube. Thus upon inflation of the annular balloon the passage of the stomach contents into the esophagus will be prevented and the entry of air into the stomach at atmospheric pressure through the third tube will equalize the pressure within the stomach during the removal of the contents by suction through the first tube.

The present invention provides a gastric tube which can also be used for gavage or for the introduction or attachment of medical devices such as an esophageal stethoscope or esophageal temperature probe.

The foregoing and other objects features and advantages of the invention will be apparent from the following more particular description of a preferred embodiment of the invention as illustrated in the accompanying drawings.

DETAILED DESCRIPTION OF THE INVENTION

Figure 1:
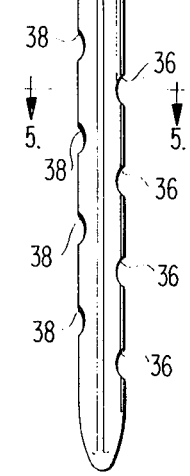
FIG. 1 is a perspective view of the oral-nasal gastric tube according to the present invention.

The tube 10 as shown in FIG. 1 will vary in length depending upon the size of the patient. In practice the tube will be manufactured in three general sizes for infants, children and adults although specialized tubes of any desired length could readily be manufactured. The principle portion of the tube from the point A to the point B is divided into three separate, independent internal passages 12, 14 and 16 by means of an integral internal Y-shaped divider 18. The tube should be rigid enough to be introduced into the stomach through the nose or mouth but be as flexible as possible to cause the least trauma to the patient during introduction. Thus the tube would preferably be made from rubber, polyvinyl chloride, polyethylene, silastic, latex or a combination of these materials. The tube 10 could be extruded to achieve the three passages or three separate individual tubes could be bonded together into a single envelope to accomplish the same purpose.

At the outermost end of the tube 10, that is the end of the tube which is adapted to extend outwardly of the patient, the tube is separated into three separate tubes 20, 22 and 24 which are continuations of the passages 12, 14 and 16 respectively.

An elastic cuff or annular balloon 26 is secured to the tube 10 at spaced apart locations 28 and 30. The balloon 26 may be of thin flexible plastic or rubber material which may be bonded or vulcanized to the tube 10 in any suitable air-tight manner. The passage 16 terminates between the ends 28 and 30 of the balloon 26 and is disposed in communication with the interior of the balloon 26 through aperture 32. The tube 24 which is a continuation of the passage 16 can be connected to a source of pressurized air or water having suitable valve control means to control the inflation and deflation of the balloon 26. The balloon 26 can also be inflated with a syringe and kept inflated with a small surgical clamp on the tube 24. The tube 10 from the point B where the passage 16 terminates to the innermost end C of the tube consists only of the passages 12 and 14 which are divided by an integral diametrically extending wall 34. The passage 14 is provided with a plurality of apetures 36 and the passage 12 is provided with a plurality of apertures 38 adjacent the innermost end C. Thus when the tube 22, which is an extension of the passage 14 is connected to a suction device the contents of the stomach can be drawn into the passage 14 through the apertures 36 for removal. The tube 20 which is an extension of the passage 12 can be left open to atmospheric air pressure so that air under atmospheric pressure will be introduced into the stomach through the apertures 38 to equalize the pressure in the stomach as the contents thereof are being withdrawn through the suction tube 22.

Figure 2:
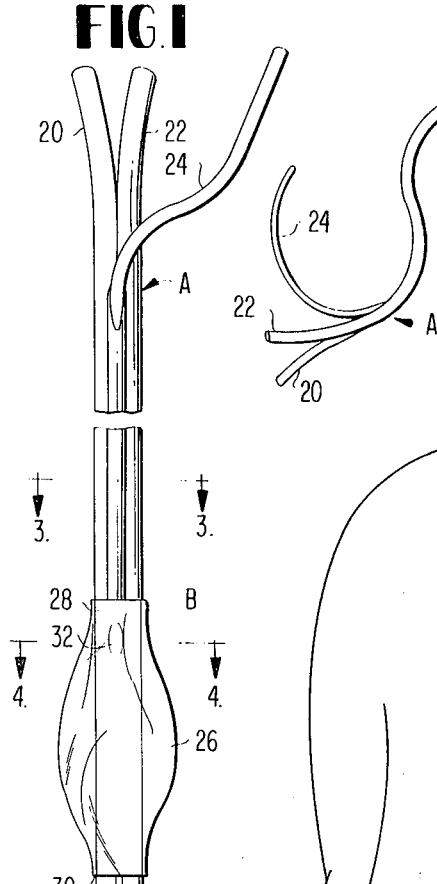
FIG. 2 is a schematic showing of a oral-nasal gastric tube of the present invention in position in a patient through the oral cavity.
Figure 2:
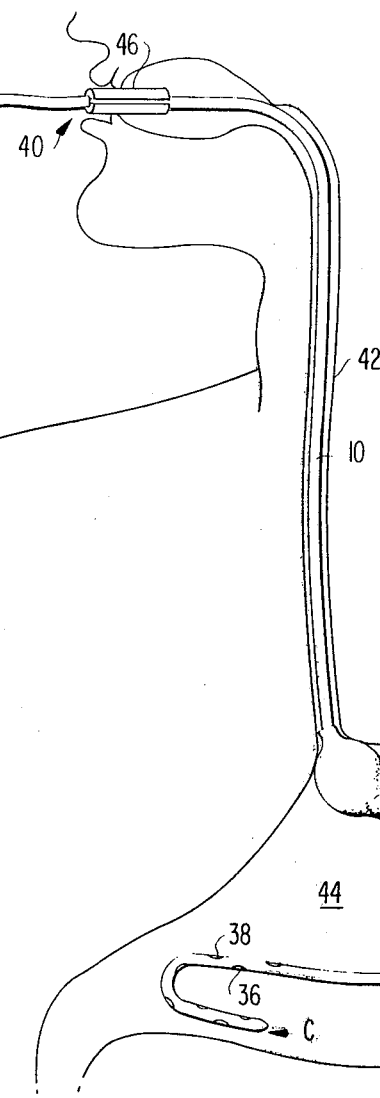
Figure 3:
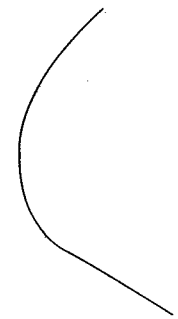
FIG. 3 is a sectional view of the tube taken along the line 3—3 of FIG. 1.
Figure 3:
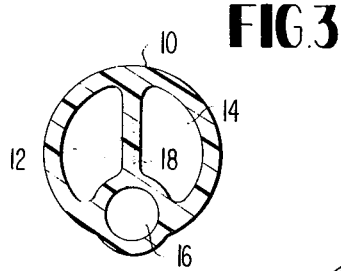
Figure 5:
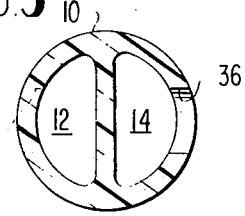
FIG. 5 is a sectional view of the tube taken along the line 5—5 of FIG. 1.
Figure 4:
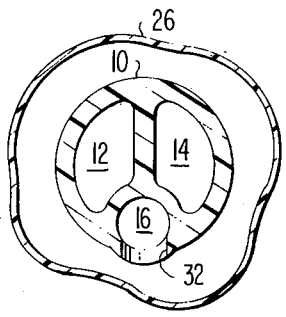
FIG. 4 is a sectional view of the tube taken along the line 4—4 of FIG. 1.

As best shown in FIG. 2 the tube 10 is adapted to be inserted through the mouth 40 down the esophagus 42 and into the stomach 44. The balloon 26 is inflated to seal off the esophagus at its junction with the stomach to prevent the vomiting or aspiration of the contents of the stomach to the esophagus. The bite block 46 which consists of a split sleeve of relatively hard rubber, plastic or other suitable material can be disposed about the tube where it passes into the mouth of the patient to prevent the patient from biting down on the tube and closing one or more of the internal passages or otherwise damaging the tube.

Although the tube 20 may be left open to the atmosphere for the purose of equalizing the pressure within the stomach cavity during the removal of the stomach contents by suction through the tube 22 the tube 20 can at other times be utilized for gavage or for the introduction or attachment of other medical devices such as an esophageal stethoscope or an esophageal temperature probe. The tube can also be used in the Trendelenburg position to prevent the stomach contents from getting into the air ways. The tube greatly expedites the emptying of the stomach contents without the danger of aspiration following ingestion of poisons or drug overdoses by continuous gavage and suction. It is also possible to attach micro-electronic devices to the stomach portion of the tube for heart monitoring, visualization and the like. In addition to inserting the tube 10 through the mouth it may also be inserted through the nasal passages.

The tube according to the present invention is relatively inexpensive and disposable. Thus the tube in a variety of sizes can be readily made available in every operating room, in lifesaving vehicles such as ambulances, helicopters and the like, by every pool side for use in the rapid resuscitation of drowning victims as well as in every first aid station. The use of the disposable tube according to the present invention can easily be taught to all para-medical personnel such as nurses, medics, ambulance personnel, lifeguards and the like.

For routine gall bladder surgery, this tube can relieve the stomach of accumulated bile the acidity of which can cause extensive lung damage when aspirated. The tube can evacuate and clean a bleeding stomach which will enable the surgeon to locate the site and amount of damage of the bleeding area, take a biopsy of tissue, or preform other necessary surgical procedures. The tube is able to be used in unconscious and paralyzed patients. Age and size of patients are irrelevant. Neonates of a few weeks age are easily administered this device, e.g. in resuscitation. The most obvious anesthesia benefit is with the emergency "full stomach" patient, i.e. one who has not been surgically prepared by discontinuance of anything by mouth for several hours before surgery. Uncontrollable vomiting and aspiration of unknown quantities and substances of stomach frequently cause death or extended intensive care unit utilization, lengthy therapy to clean the lung(s) or recover collapsed lung(s), and lengthy recuperation at great financial expense as well as physical and emotional suffering.

While the invention has been particularly shown and described with reference to a preferred embodiment thereof it will be understood by those in the art that various changes in form and details may be made therein without departing from the spirit and scope of the invention.

What is claimed is:

1. A flexible oral nasal gastric tube adaptable for insertion into the stomach of a patient through the esophagus comprising first and second independent parallel passages disposed within said tube and extending the entire length thereof, aperture means disposed only adjacent the end of the tube adapted to be inserted into the stomach for communicating the first and second passages with the stomach cavity, single annular inflatable means disposed about the periphery of said tube at a location spaced a substantial distance from said aperture means in said tube disposed in communication with the interior of said inflatable means; said inflatable means being spaced from said aperture means a substantial distance so that when said annular inflatable means is inflated within the stomach and disposed in sealing contact with the area of the stomach surrounding the entrance of the esophagus into the stomach to prevent regurgitation, the end of the tube having the aperture means will be disposed in the bottom of the stomach, each of said passages being connected to separate individual tubes adjacent the end of the tube opposite the end having the aperture means whereby the tube connected to the third passage can be connected to a fluid source for the selective inflation and deflation of said inflatable means, the tube connected to the first passage can be connected to suitable suction means for removing the contents of the stomach and the tube connected to the second passage can be disposed in communication with the atmosphere.

2. A tube as set forth in claim 1 wherein said passages in said tube are defined by partition means which are of integral one piece construction with said tube.

3. A tube as set forth in claim 1 wherein said inflatable means is comprised of an annular sheath of elastomeric material secured at opposite ends to the exterior surface of said tube.

4. A tube as set forth in claim 1 further comprising bite block means detachably secured to said tube to prevent damage by the patient's teeth.

* * * * *